(12) United States Patent
Tsai et al.

(10) Patent No.: US 10,967,013 B2
(45) Date of Patent: Apr. 6, 2021

(54) LACTIC ACID BACTERIUM FOR PROPHYLAXIS OR TREATMENT OF A STRESS-INDUCED DISORDER AND A COMPOSITION CONTAINING THE SAME

(71) Applicant: National Yang-Ming University, Taipei (TW)

(72) Inventors: Ying-Chieh Tsai, Taipei (TW); Wei-Hsien Liu, Taipei (TW); Yi-Chen Juan, Taipei (TW); Chien-Chen Wu, Taipei (TW)

(73) Assignee: National Yang-Ming University, Taipei (TW)

( * ) Notice: Subject to any disclaimer, the term of this patent is extended or adjusted under 35 U.S.C. 154(b) by 0 days.

(21) Appl. No.: 14/259,442

(22) Filed: Apr. 23, 2014

(65) Prior Publication Data

US 2015/0306157 A1 Oct. 29, 2015

(51) Int. Cl.
*A61K 35/747* (2015.01)
*C12R 1/25* (2006.01)
*A61K 35/00* (2006.01)

(52) U.S. Cl.
CPC .............. *A61K 35/747* (2013.01); *C12R 1/25* (2013.01); *A61K 2035/11* (2013.01)

(58) Field of Classification Search
CPC ......... A61P 25/00; C12R 1/25; A61K 35/747; A61K 2035/11
See application file for complete search history.

(56) References Cited

U.S. PATENT DOCUMENTS

2013/0101566 A1* 4/2013 Espadaler Mazo .... A61K 35/74
424/93.21

OTHER PUBLICATIONS

Chao et al., Diversity of lactic acid bacteria in suan-tsai and fu-tsai, traditional fermented mustard products of Taiwan, International Journal of Food Microbiology 135 (2009) 203-210.*
Ducrotte et al., Clinical trial: Lactobacillus plantarum 299v (DSM 9843) improves symptoms of irritable bowel syndrome , World J Gastroenterol Aug. 14, 2012; 18(30): 4012-4018.*
Bousvaros, Can probiotics help treat depression and anxiety, Harvard Health Blog, https://www.health.harvard.edu/blog/can-probiotics-help-treat-depression-anxiety-2017072612085, last visited Nov. 29, 2018.*
Berger et al., The relationship between plasma corticosterone levels and leverpress avoidance vs escape behaviors in rats, Physiological Psychology, 1981, vol. 9 (1) 81-96.*
Reardon, Depression researchers rethink popular mouse swim tests, Springer Nature (2020).*

(Continued)

*Primary Examiner* — Sean C. Barron
(74) *Attorney, Agent, or Firm* — McCarter & English, LLP

(57) ABSTRACT

The present invention provides an isolated lactic acid bacterium, *Lactobacillus plantarum* subsp. *plantarum* PS128 deposited under DSMZ Accession No. DSM 28632, for prophylaxis or treatment of a stress-induced disorder. The present invention further provides a composition for prophylaxis or treatment of a stress-induced disorder that comprises *Lactobacillus plantarum* subsp. *plantarum* PS128. Moreover, the present invention provides a method for prophylaxis or treatment of a stress-induced disorder in a subject that comprises a step of administering an effective amount of *Lactobacillus plantarum* subsp. *plantarum* PS128 to the subject.

4 Claims, 3 Drawing Sheets
Specification includes a Sequence Listing.

(56) References Cited

OTHER PUBLICATIONS

Menke, Is the HPA Axis as Target for Depression Outdated, or Is There a New Hope?, Front. Psychiatry 10: 101 (2019).* https://clinicaltrials.gov/ct2/show/NCT02469545 (2015).*

Castagne et al. Rodent Models of Depression: Forced UNIT 8.10A Swim and Tail Suspension Behavioral Despair Tests in Rats and Mice. Curr. Protoc. Neurosci (2011). 55:8.10A.1-8.10A.14. (Year: 2011).*

McCormick et al. From the Stressed Adolescent to the Anxious and Depressed Adult: Investigations in Rodent Models. Neuroscience (2013), 249, 242-257. (Year: 2013).*

Uher et al. Self-Report and Clinician-Rated Measures of Depression Severity: Can One Replace the Other? Depress. Anxiety (2012), 29(12), 15 page manuscript. (Year: 2012).*

Liu et al. Psychotropic effectsof Lactobacillus plantarum PS128 in earlylife-stressed and naïve adult mice. Brain Research (2016), 1631, 1-12. (Year: 2016).*

\* cited by examiner

SEQUENCE LISTING

<160> NUMBER OF SEQ ID NOS: 2

<210> SEQ ID NO 1

```
<211> LENGTH: 22
<212> TYPE: DNA
<213> ORGANISM: Artificial
<220> FEATURE:
<223> OTHER INFORMATION: primer for ERIC-PCR
<220> FEATURE:
<221> NAME/KEY: misc_difference
<222> LOCATION: (1)..(22)

<400> SEQUENCE: 1
atgtaagctc ctggggattc ac                                            22

<210> SEQ ID NO 2
<211> LENGTH: 22
<212> TYPE: DNA
<213> ORGANISM: Artificial
<220> FEATURE:
<223> OTHER INFORMATION: primer for ERIC-PCR
<220> FEATURE:
<221> NAME/KEY: misc_difference
<222> LOCATION: (1)..(22)

<400> SEQUENCE: 2
aagtaagtga ctggggtgag cg                                            22
```

LACTIC ACID BACTERIUM FOR PROPHYLAXIS OR TREATMENT OF A STRESS-INDUCED DISORDER AND A COMPOSITION CONTAINING THE SAME

BACKGROUND OF THE INVENTION

1. Field of the Invention

This invention relates to a lactic acid bacterium, and more particularly relates to a novel lactic acid bacterium strain for prophylaxis or treatment of a stress-induced disorder in a subject.

2. Description of Related Art

Lactic acid bacteria (hereinafter, referred to LAB) have not only been recognized as alternatives of prevention or treatment for gut health because of their capability in regulating host's gut microbiota, in recent years, the increased evidences also emerge that LAB are able to alter host's mental and physical responses for psychological stress.

Stress is one of the factors inducing mood disorders and neurochemical changes in both human and animals. Rodents subjected to forced-swimming as an acute stressor often show increased immobility in the re-test on next day. Studies have shown that exposing rodents to early life stress by maternal deprivation leads to multiple abnormalities including intestinal inflammations, anxiety-like and depression-like behaviors in adulthood, impaired function of hypothalamus-pituitary-adrenal (HPA) axis, and altered neurotransmitters compared to their normal-reared controls. Stress-induced disorders include, but are not limited to anxiety, depression and irritable bowel syndrome.

Treatment of stress-induced disorders by LAB might be a supplement except conventional psychiatric medicines as LAB have been shown to have an influence on host gut-brain axis (GBA). It was demonstrated that germ-free mice lack the increased motor activity and reduced anxiety had put the emphasis on the key role of normal gut microbiota in brain development. Previous study showed that *Lactobacillus rhamnosus* altered functions of central nerve system in healthy mice through vagus nerve, and the maternal separated rats with probiotic strain *Bifidobacterium infantis* had reversed the behavioral deficits in forced swimming test (FST) and restored basal noradrenaline (NA) level in brain-stem. The above-mentioned studies support that probiotics might be developed as treatment on psychiatric disorders and neurotransmitter.

SUMMARY OF THE INVENTION

The present invention provides an isolated lactic acid bacterium, which is *Lactobacillus plantarum* subsp. *plantarum* PS128 and deposited under DSMZ Accession No. DSM 28632. In one aspect of the present application, a composition that comprises *Lactobacillus plantarum* subsp. *plantarum* PS128 and a carrier is provided.

In certain embodiments, the carrier comprises glycerol, such as 10-15% (e.g., 12.5%) glycerol.

In certain embodiments, the carrier comprises a growth medium, such as a growth medium suitable for supporting LAB growth. For example, the growth medium may be the Man Rogosa Sharpe (MRS) broth (see deMan, Rogosa and Sharpe. 1960. *J. Appl. Bacteriol.* 23:130, incorporated herein by reference), which is commercially available from numerous venders. See DIFCO™ Lactobacilli MRS Broth (Cat. No. 288110, 288120, and 288130).

| Approximate Formula* Per Liter of DIFCO ™ Lactobacilli MRS Broth: | |
|---|---|
| Proteose Peptone No. 3 | 10.0 g |
| Beef Extract | 10.0 g |
| Yeast Extract | 5.0 g |
| Dextrose | 20.0 g |
| Polysorbate 80 | 1.0 g |
| Ammonium Citrate | 2.0 g |
| Sodium Acetate | 5.0 g |
| Magnesium Sulfate | 0.1 g |
| Manganese Sulfate | 0.05 g |
| Dipotassium Phosphate | 2.0 g |

*Adjusted and/or supplemented as required to meet performance criteria.

In certain embodiments, the composition is prepared by inoculating *Lactobacillus plantarum* subsp. *plantarum* PS128 in a culture suitable to support growth of PS128; fermenting the culture; and harvesting *Lactobacillus plantarum* subsp. *plantarum* PS128 as pellets. The culture can be the MRS Broth, or a medium comprising one or more carbohydrate substrates tested to be able to support (e.g., "+") fermentation of *Lactobacillus plantarum* subsp. *plantarum* PS128 in Example 2.

The preparation may further comprise adjusting the final colony formation unit (CFU) per milliliter with a growth medium (e.g., MRS broth) and/or glycerol (e.g., 12.5%) to $1\times10^9$ CFU/mL, $2\times10^9$ CFU/mL, $3\times10^9$ CFU/mL, $4\times10^9$ CFU/mL, $5\times10^9$ CFU/mL, $6\times10^9$ CFU/mL, $7\times10^9$ CFU/mL, $8\times10^9$ CFU/mL, $9\times10^9$ CFU/mL, or $10\times10^9$ CFU/mL.

In one aspect of the present application, a method for treating or preventing a stress-induced disorder in a subject that comprises a step of administering an effective amount of *Lactobacillus plantarum* subsp. *plantarum* PS128 to the subject is provided. Preferably, the lactic acid bacterium is orally-administered to the subject.

In one embodiment, the stress-induced disorder is selected from the group consisting of anxiety, depression and irritable bowel syndrome.

In a further embodiment, after the administration of *Lactobacillus plantarum* subsp. *plantarum* PS128, a serum corticosterone level is statistically significant decreased in the subject. Moreover, after the administration of *Lactobacillus plantarum* subsp. *plantarum* PS128, a neurotransmitter level is statistically significant increased in the subject. Preferably, the neurotransmitter is selected from the group consisting of dopamine (DA), dihydroxyphenylacetic acid (DC), and homo-vanillic acid (HVA).

In another aspect of the present application, a method for treating or preventing a psychiatric disorder in a subject that comprises a step of administering an effective amount of *Lactobacillus plantarum* subsp. *plantarum* PS128 to the subject is provided. Preferably, the lactic acid bacterium is orally-administered to the subject.

In one embodiment, the psychiatric disorder is selected from the group consisting of anxiety, depression and irritable bowel syndrome.

In a further embodiment of the present application, after the administration of *Lactobacillus plantarum* subsp. *plantarum* PS128, a serum corticosterone level is statistically significant decreased in the subject. Moreover, after the administration of *Lactobacillus plantarum* subsp. *plantarum* PS128, a neurotransmitter level is statistically significant increased in the subject. Preferably, the neurotransmitter is selected from the group consisting of dopamine, dihydroxyphenylacetic acid, and homo-vanillic acid.

Figure 2:
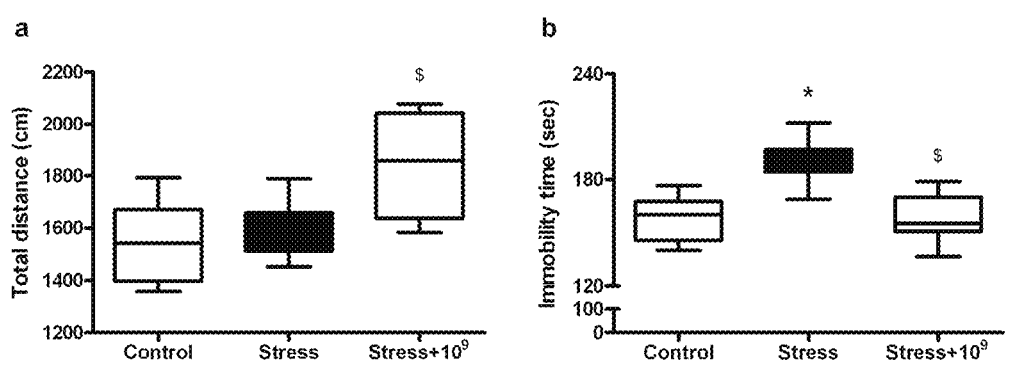

FIGS. 2A-2B show that *Lactobacillus plantarum* subsp. *plantarum* PS128 increases total distance moved in the open field test and normalizes depression-like behavior in the forced swimming test of the mice. * $p<0.05$ compared to CONTROL group; $ $p<0.05$ compared to STRESS group.

Figure 3:
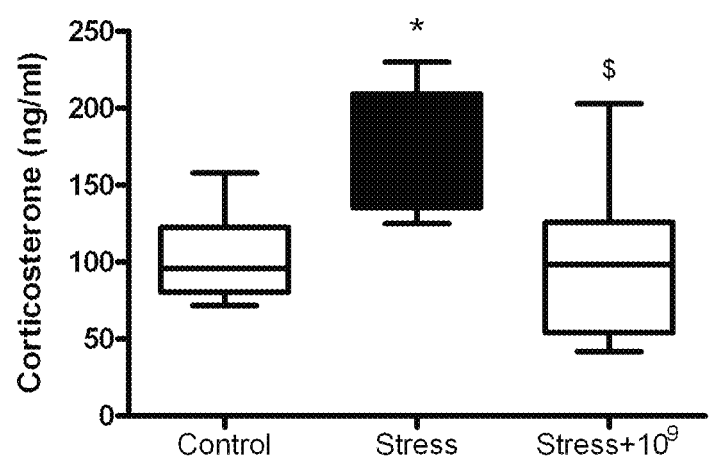

FIG. 3 shows the concentration of serum corticosterone. * $p<0.05$ compared to CONTROL group; $ $p<0.05$ compared to STRESS group.

Figure 4:
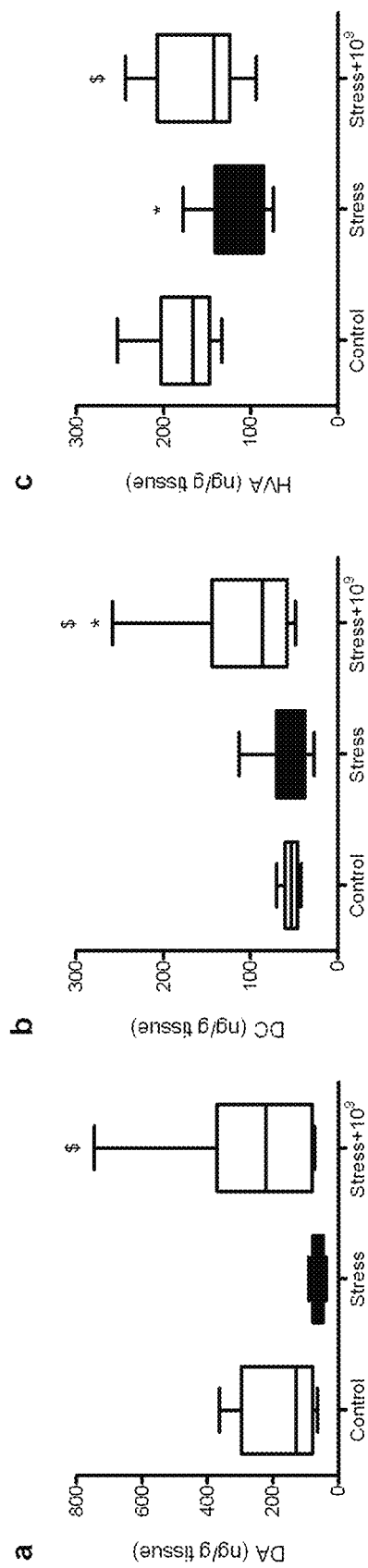

FIGS. 4A-4C show alterations of *Lactobacillus plantarum* subsp. *plantarum* PS128 on prefrontal cortical dopaminergic and serotonergic pathway of mice. * $p<0.05$ compared to CONTROL group; $ $p<0.05$ compared to STRESS group.

DETAILED DESCRIPTION OF THE INVENTION

The following specific examples are used for illustrating the present invention and are not limiting. A person skilled in the art can easily conceive the other advantages and effects of the present invention. The present invention can also be implemented by different specific cases be enacted or application, the details of the instructions can also be based on different perspectives and applications in various modifications and changes do not depart from the spirit of the creation.

Many examples have been used to illustrate the present invention. The examples sited below should not be taken as a limit to the scope of the invention.

EXAMPLES

Example 1

Isolation of *Lactobacillus plantarum* Subsp. *Plantarum* PS128 and Identification of the Bacterial Strains Using PCR-Fingerprinting

*Lactobacillus plantarum* subsp. *plantarum* PS128 (hereinafter referred to PS128) was isolated from fu-tsai, traditional fermented mustard products of Taiwan.

ERIC-PCR was conducted to further distinguish the subspecies of bacteria with high sequence similarity.

Figure 1:
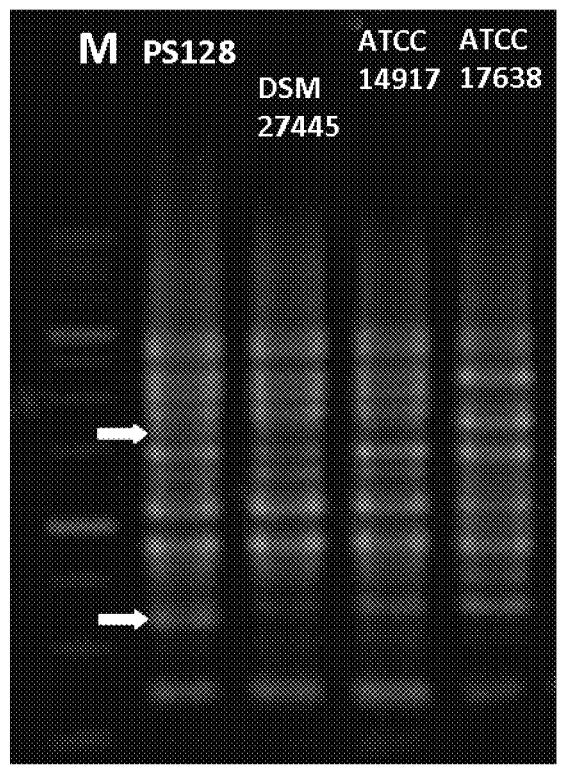
FIG. 1 is an electrophoresis photograph showing the PCR-fingerprinting profiles of *Lactobacillus plantarum* strains, wherein M represents DNA ladder; DSM 27445 represents *Lactobacillus plantarum* subsp. *plantarum*; ATCC 14917$^T$ represents *Lactobacillus plantarum* subsp. *plantarum*; and ATCC 17638$^T$ represents *Lactobacillus plantarum* subsp. *argentoratensis*.

The PCR-fingerprinting profile of PS128 was carried out under the condition indicated in Table 1. DNAs extracted from this strain were used as templates. The obtained amplification products were electrophoresed and the patterns were compared as shown in FIG. 1, wherein the primers represented by SEQ ID NO: 1 and SEQ ID NO: 2 were used.

SEQ ID NO: 1
ERIC1R: (5'-ATGTAAGCTCCTGGGGATTCAC-3')

SEQ ID NO: 2
ERIC2: (5'-AAGTAAGTGACTGGGGTGAGCG-3')

TABLE 1

Composition of the PCR reaction solution (25 μl per PCR tube)

| Component | Volume |
|---|---|
| ddH$_2$O | 16.3 μl |
| 10X PCR Buffer | 2.5 μl |
| dNTP | 2.0 μl |
| MgCl$_2$ (25 mM) | 1.0 μl |
| primer (GTG)$_5$ (10 μM) | 2.0 μl |
| rTaq polymerase | 0.2 μl |
| DNA template (10 μM) | 1.0 μl |

TABLE 2

PCR Conditions

| Temperature | Time | Cycle |
|---|---|---|
| 94° C. | 5 min | |
| 94° C. | 30 sec | 35 cycles |
| 45° C. | 1 min | |
| 65° C. | 6 min | |
| 65° C. | 10 min | |

As shown in FIG. 1, Lane M represents DNA ladder (250-10000 bp); DSM 27445 represents *Lactobacillus plantarum* subsp. *plantarum*; ATCC 14917$^T$ represents *Lactobacillus plantarum* subsp. *plantarum*; and ATCC 17638$^T$ represents *Lactobacillus plantarum* subsp. *argentoratensis*.

As indicated by white arrows, the bands of PS128 are unique in position among those of DSM 27445, ATCC 14917 or ATCC 17638 and hence the result in FIG. 1 shows that even though PS128, DSM227445 and ATCC14917$^T$ all belong to *Lactobacillus plantarum* subsp. *plantarum*, they are still different bacterial strains. Consequently, PS128 represented a new strain of *Lactobacillus plantarum* subsp. *plantarum*.

*Lactobacillus plantarum* subsp. *plantarum* PS128 has been deposited under Budapest Treaty at Leibniz Institute DSMZ-German Collection of Microorganisms and Cell Cultures (Inhoffenstr. 7 B, D-38124 Braunschweig, Germany) on Mar. 31, 2014 and has been given the DSMZ Accession No. DSM 28632 by the International Depositary Authority. This biological material was subjected to the viability test and passed.

Example 2

Analytical Profile Index (API) Typing

Sugar utilization for PS128 used in the present invention was investigated using API50CHL kit (bioMerieux, France), and the results are shown in Table 3. The fermentation test indicates that PS128 harbor a biochemical property similar to *Lactobacillus plantarum* subsp. *plantarum*.

TABLE 3

Results of Fermentation Test$^a$

| Carbohydrates Substrate Strips | PS128 |
|---|---|
| CONTROL | |
| Glycerol | |
| Erythritol | |
| D-Arabinose | |
| L-Arabinose | |
| D-Ribose | |
| D-Xylose | |

TABLE 3-continued

Results of Fermentation Test[a]

| Carbohydrates Substrate Strips | PS128 |
|---|---|
| L-Xylose | |
| D-Adonitol | |
| Methyl-β-D-Xylopyranoside | |
| D-Galactose | |
| D-Glucose | |
| D-Fructose | |
| D-Mannose | |
| L-Sorbose | |
| L-Rhamnose | |
| Dulcitol | |
| Inositol | |
| D-Mannitol | |
| D-Sorbitol | |
| Methyl-α-D-mannopyranoside | |
| Methyl-α-D-glucopyranoside | |
| N-Acetyl glucosamine | |
| Amygdalin | |
| Arbutin | |
| Esculin ferric citrate | |
| Salicin | |
| D-Cellobiose | |
| D-Maltose | |
| D-Lactose (bovine origin) | |
| D-Melibiose | |
| D-Saccharose (sucrose) | |
| D-Trehalose | |
| Inulin | |
| D-Melezitose | |
| D-Raffinose | |
| Amidon (starch) | |
| Glycogen | |
| Xylitol | |
| Gentiobiose | |
| D-Turanose | |
| D-Lyxose | |
| D-Tagatose | |
| D-Fucose | |
| L-Fucose | |
| D-Arabitol | |
| L-Arabitol | |
| Potassium gluconate | |
| Potassium 2-ketogluconate | |
| Potassium 5-ketogluconate | |

[a]+, positive; −, negative;

Example 3

Alternations of Behaviors, Stress Hormone and Neurotransmitter Levels in Stressed Mice by *Lactobacillus plantarum* subsp. *plantarum* PS128

(1) Preparation of Lactic Acid Bacteria

LAB was inoculated in Man Rogosa Sharpe (MRS, BD, USA) broth, cultured at 37° C. for 18 hrs and harvested by centrifugation at 6000×g for 10 mins. Pellets were resuspended to a final concentration of $5\times10^9$ or $5\times10^9$ colony formation unit (CFU) per milliliter by fresh MRS containing 12.5% glycerol and stored at −20° C. until use.

(2) Animals and Housing

Eight-week-old Male C57BL/6JNarl or timed-pregnant C57BL/6JNarl were purchased from National Laboratory Animal Center (NLAC, Taipei, Taiwan) and housed in filter-top cages with chow diet (LabDiet Autoclavable Rodent Diet 5010, PMI Nutrition International, Brentwood, USA) and water ad libitum in a specific pathogen-free room at Laboratory Animal Center, National Yang-Ming University under standard condition (temperature 22° C., 50-60% humidity and 12-h light/dark cycle) for approximately one week until delivery. All animal experimental procedures were reviewed and approved by the Animal Management Committee, National Yang-Ming University.

(3) Early Life Stress

Early life stress by maternal deprivation under hypothermal environment was modified from previous studies (Millstein and Holmes 2007, Desbonnet, Garrett et al. 2010). Briefly, neonatal were separated from their mothers and littermates 3 h (11:00-14:00) daily between postnatal day (PD) 2-14 under room temperature (~22° C.). Followed by 2 weeks of undisturbed except bedding change once per week, the stressed pups were weaned and randomly assigned to 5-6 mice per cage. Only male pups were used for experiment (n=12 for STRESS groups, n=12 for STRESS+ $10^9$). The mice that did not receive early life stress were served as control group (CONTROL, n=10).

(4) Experimental Design and Sampling

Mice were administrated with saline or PS128 ($10^9$ CFU/mouse/day) for 4 weeks from weaning (PD28) to the age of 8-weeks-old. They underwent a battery of behavioral tests including OFT and FST sequenced from the least to the most stressful ones conducted in light phase. On the day of sacrifice, mice were subjected to a short forced swimming as a stressor 30 min prior to retro-orbital blood collection followed cervical dislocation which all took place between 11:00 and 14:00 h to minimize the effects of circadian rhythm. Brain were quickly removed and specific region prefrontal cortex was dissected on ice and frozen in liquid nitrogen or preserved in 0.6% perchloric acid buffer, then stored at −80° C. until use.

(5) Open Field Test (OFT)

The open field test (OFT) is a common measure of exploratory behavior and general activity in both mice and rats, where both the quality and quantity of the activity can be measured.

Locomotor activity was monitored and calculated by an open field activity system (Tru Scan activity system, Coulbourn Instruments, PA, USA) comprised of one arena (25.4× 25.4×38 cm) with two photobeam sensor rings outside of the Plexiglas wall. Each mouse was placed into the same corner of the arena for 10 min to measure several activities including total distance moved. The box was cleaned with water and 70% ethanol after each run, and the mouse was returned to its home cage. The activities were automatically recorded and quantified by the Tru Scan 2.2 software (Coulbourn Instruments).

(6) Forced Swimming Test (FST)

The forced swimming test is a rodent behavioral test used for evaluation of antidepressant drugs, antidepressant efficacy of new compounds, and experimental manipulations that are aimed at rendering or preventing depressive-like states.

FST were assessed as previously described (Cryan, Dalvi et al. 2001) with modifications. Briefly, immobility was calculated 4 min (1-5 min) of a single 6-min forced swimming test which the mice were put in a transparent acrylic cylinder (30 cm height×10 cm internal diameter, containing 15 cm-depth water with temperature adjusted to 23±1° C.), recorded by a camera and further analyzed by a video tracking software EthoVision (Noldus Information Technology, Wageningen, The Netherlands). Mice were dried with tissue paper after tested and returned to their home cage. Transparent acrylic cylinders (30 cm height×10 cm internal diameter) containing 15 cm-depth water with temperature adjusted to 23-25° C. were used for a single 6-min trial. The behaviors were recorded by a video camera. A video tracking software EthoVision (Noldus Information Technology, Wageningen, The Netherlands) was used for analysis.

Immobility was calculated for 1 to 5 min with the same parameters to avoid human errors. Mice were dried with tissue paper after tested and returned to their home cage.

As shown in FIGS. 2A-2B, in the OFT, the stressed mice had similar total distance moved compared to CONTROL (FIG. 2A) while they had greater time of immobile in FST (FIG. 2B). Administration of PS128 to the stressed mice significantly increased the total distance moved in the OFT and decreased the immobility in the FST (FIGS. 2A and 2B) to the degrees similar to CONTROL mice. * p<0.05 compared to CONTROL group; $ p<0.05 compared to STRESS group.

(7) Determination of Serum Corticosterone

Plasma corticosterone level is an indicator the activation of the hypothalamic-pituitary-adrenal axis, the basic response in body-brain interaction under stress or fear.

Serum was obtained from blood samples centrifuged at 4° C., 3000×g for 10 min that were collected from mice under normal state or 30 min after forced swimming between 11:00 to 14:00 to reduce the effects of circadian rhythm. Serum was properly diluted and then applied to a commercial CORT EIA kit (Cayman, USA), concentrations were interpolated by standards provided by the kit.

As shown in FIG. 3, by measuring the serum level, the inventors found that corticosterone was significantly elevated in the stressed mice and was reversed by the administration of PS128 (stress+$10^9$). * p<0.05 compared to CONTROL group; $ p<0.05 compared to STRESS group.

(8) Quantification of Monoamines and their Metabolites by HPLC-ED

HPLC-ECD has the high performance for routine measurements of biological or environmental samples such as catecholamines (dopamine, norepinephrine, and epinephrine), monoamines (e.g., serotonin, dopamine, norepinephrine, and epinephrine) acetylcholine, glutamate, glycine, GABA, and others.

The neurotransmitters to be measured include dopamine (DA), dihydroxyphenylacetic acid (DC) and homo-vanillic acid (HVA). The high performance liquid chromatography-electrochemical detector (HPLC-ED) system comprised a micropump (CMA-100, CMA, Stockholm, Sweden), an on-line injector (CMA-160), a Microtech LC-pump (Microtech Scientific, Sunnyvale, Calif.), and BAS-4C electrochemical detector (Bioanalytical Systems, Inc., West Lafeyette, Ind.) as previously described (Cheng, Kuo et al. 2000). A reversed-phase column (Kinetex $C_{18}$, 2.6 um, 100×2.1 mm I.D., Phenomenex, USA) was used for analysis. The potential for the glassy carbon working electrode was set at +650 mV with respect to a Ag/AgCl reference electrode at room temperature (25° C.). The mobile phase containing 0.1 M $NaH_2PO4$, 8% methanol, 0.74 mM SOS, 0.03 mM EDTA and 2 mM KCl, was adjusted to pH 3.74 with $H_3PO_4$. Whole brains were frozen on dry ice immediately after collected from cervical dislocated mice. Prefrontal cortex was dissected and preserved in 0.6% perchloric acid buffer and stored at −80° C. until homogenized by sonication and centrifuged at 12000×g, 10 min. Supernatants were filtered by 0.22 m PVDF membrane (4 mm syringe filter, Millex-GV, Millipore, USA) before analyze. Properly diluted supernatants were injected (20 µl) into the chromatographic system at a flow rate of 0.2 ml/min. The concentrations of monoamines were interpolated by the following standards: DA, DC and HVA (Sigma-Aldrich, St. Louis, Mo., USA) ranged from 1 to 100 ng/ml.

As shown in FIGS. 4A-4C, by applying the early life stress protocol, neurotransmitters in prefrontal cortex was altered. In the dopaminergic pathway, dopamine itself was reduced and the level of its metabolite DC was similar to that of CONTROL group (FIGS. 4A and 4B) while the other metabolite HVA was significantly decreased (FIG. 4C). Administration of PS128 significantly increased dopamine, DC and HVA levels of the stressed mice (FIG. 4A-4C). * p<0.05 compared to CONTROL group; $ p<0.05 compared to STRESS group.

Example 5

Statistical Analysis

All data presented herein were expressed as means±the standard deviation (SD). Statistical analysis was calculated by one-way ANOVA followed by a Bonferroni post-hoc test. Statistical difference between groups denoted by asterisk (*) or dollar sign ($) if p <0.05.

The present invention finds a potential strain, *Lactobacillus plantarum* subsp. *plantarum* PS128, that exerts benefits on stressed mice and is reported that by administrating a *Lactobacillus* strain PS128, behaviors of the mice were improved.

While some of the embodiments of the present invention have been described in detail in the above, it is, however, possible for those of ordinary skill in the art to make various modifications and changes to the particular embodiments shown without substantially departing from the teaching and advantages of the present invention. Such modifications and changes are encompassed in the spirit and scope of the present invention as set forth in the appended claim.

The references listed below and the ATCC numbers cited in the application are each incorporated by reference as if they were incorporated individually.

1. Cheng, F. C., J. S. Kuo, H. M. Huang, D. Y. Yang, T. F. Wu and T. H. Tsai (2000), "Determination of catecholamines in pheochromocytoma cell (PC-12) culture medium by microdialysis-microbore liquid chromatography," *J. Chromatogr. A.*, 870(1-2): 405-411.
2. Cryan, J. F., A. Dalvi, S. H. Jin, B. R. Hirsch, I. Lucki and S. A. Thomas (2001), "Use of dopamine-beta-hydroxylase-deficient mice to determine the role of norepinephrine in the mechanism of action of antidepressant drugs," *J. Pharmacol. Exp. Ther.*, 298(2): 651-657.
3. Desbonnet, L., L. Garrett, G Clarke, B. Kiely, J. F. Cryan and T. G Dinan (2010), "Effects of the probiotic *Bifidobacterium infantis* in the maternal separation model of depression," *Neuroscience*, 170(4): 1179-1188.
4. Millstein, R. A. and A. Holmes (2007), "Effects of repeated maternal separation on anxiety- and depression-related phenotypes in different mouse strains," *Neurosci. Biobehav. Rev.*, 31(1): 3-17.

What is claimed is:

1. A method for treating anxiety and/or depression in a subject in need thereof, comprising: administering an effective amount of a composition comprising an active agent consisting of *Lactobacillus plantarum* subsp. *plantarum* PS128.

2. The method of claim 1, wherein the composition is orally-administered to the subject.

3. A method for treating a psychiatric disorder in a subject in need thereof, comprising: administering an effective amount of a composition comprising an active agent consisting of *Lactobacillus plantarum* subsp. *plantarum* PS128 to the subject, wherein the psychiatric disorder is selected from the group consisting of anxiety and depression.

4. The method of claim 3, wherein the composition is orally-administered to the subject.

* * * * *